(12) United States Patent
Kiraly et al.

(10) Patent No.: US 10,342,620 B2
(45) Date of Patent: Jul. 9, 2019

(54) EFFICIENT TREATMENT OF ATRIAL FIBRILLATION USING THREE-DIMENSIONAL ELECTRICAL POTENTIAL MODEL

(71) Applicant: Siemens Healthcare GmbH, Erlangen (DE)

(72) Inventors: Atilla Peter Kiraly, Plainsboro, NJ (US); Tommaso Mansi, Princeton, NJ (US); Ali Kamen, Skillman, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 319 days.

(21) Appl. No.: 15/304,148

(22) PCT Filed: Apr. 9, 2015

(86) PCT No.: PCT/US2015/025020
§ 371 (c)(1),
(2) Date: Oct. 14, 2016

(87) PCT Pub. No.: WO2015/160602
PCT Pub. Date: Oct. 22, 2015

(65) Prior Publication Data
US 2017/0027649 A1 Feb. 2, 2017

Related U.S. Application Data
(60) Provisional application No. 61/979,656, filed on Apr. 15, 2014.

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/0037* (2013.01); *A61B 5/0044* (2013.01); *A61B 5/046* (2013.01);
(Continued)

(58) Field of Classification Search
USPC .......................................... 382/128, 130–132
See application file for complete search history.

(56) References Cited

U.S. PATENT DOCUMENTS 6,975,900 B2 * 12/2005 Rudy .................. A61B 5/0402
128/920
7,774,051 B2 * 8/2010 Voth ...................... A61B 5/042
600/523
(Continued)

FOREIGN PATENT DOCUMENTS

WO 20120151301 11/2012

OTHER PUBLICATIONS

PCT International Search Report and Written Opinion dated Jul. 6, 2015.
(Continued)

*Primary Examiner* — Ishrat I Sherali

(57) ABSTRACT

A method for guiding electrophysiology (EP) intervention using a patient-specific electrophysiology model includes acquiring a medical image of a patient subject (S201). Sparse EP signals are acquired over an anatomy using the medical image for guidance (S202). The sparse EP signals are interpolated using a patient specific computational electrophysiology model and a three-dimensional model of EP dynamics is generated therefrom (S203). A rendering of the three-dimensional model is displayed. Candidate intervention sites are received, effects on the EP dynamics resulting from intervention at the candidate intervention sites is
(Continued)

simulated using the model, and a rendering of the model showing the simulated effects is displayed (S205).

22 Claims, 7 Drawing Sheets

(51) Int. Cl.
*A61B 5/046* (2006.01)
*A61B 18/14* (2006.01)
*G06F 19/00* (2018.01)
*A61B 90/00* (2016.01)
*G16H 50/50* (2018.01)
*A61B 18/00* (2006.01)
*A61B 17/00* (2006.01)

(52) U.S. Cl.
CPC .......... *A61B 18/1492* (2013.01); *A61B 90/37* (2016.02); *G06F 19/00* (2013.01); *G06F 19/3481* (2013.01); *G16H 50/50* (2018.01); *A61B 2017/00053* (2013.01); *A61B 2018/00351* (2013.01); *A61B 2018/00839* (2013.01); *A61B 2034/105* (2016.02); *A61B 2090/374* (2016.02); *A61B 2090/378* (2016.02); *A61B 2090/3762* (2016.02)

(56) References Cited

U.S. PATENT DOCUMENTS

| | | | | |
|---|---|---|---|---|
| 8,041,413 | B2* | 10/2011 | Barbagli | A61B 5/06 600/424 |
| 8,057,394 | B2* | 11/2011 | Dala-Krishna | A61B 8/0883 600/466 |
| 9,277,970 | B2* | 3/2016 | Mansi | G06T 19/20 |
| 9,463,072 | B2* | 10/2016 | Comaniciu | G06T 17/20 |
| 9,589,379 | B2* | 3/2017 | Mansi | G06T 11/60 |
| 2008/0214945 | A1 | 9/2008 | Koertge et al. | |
| 2010/0268059 | A1 | 10/2010 | Ryu et al. | |
| 2014/0022250 | A1* | 1/2014 | Mansi | G06T 19/20 345/420 |
| 2014/0122048 | A1* | 5/2014 | Vadakkumpadan | A61B 5/7275 703/11 |
| 2017/0185740 | A1* | 6/2017 | Seegerer | G09B 23/288 |

OTHER PUBLICATIONS

Jazmin Aguado-Sierra, et al., "Patient-specific modeling of dyssynchronous heart failure: A case study", Progress in Biophysics and Molecular Biology, vol. 107, No. 1, Jul. 7, 2011, pp. 147-155.

* cited by examiner

501

502

EFFICIENT TREATMENT OF ATRIAL FIBRILLATION USING THREE-DIMENSIONAL ELECTRICAL POTENTIAL MODEL

CROSS-REFERENCE TO RELATED APPLICATION

The present application is based on U.S. Provisional Application Ser. No. 61/979,656, filed in the United States Patent and Trademark Office on Apr. 15, 2014, the entire contents of which are herein incorporated by reference.

TECHNICAL FIELD

The present disclosure relates to treatment of cardiac arrhythmias, like atrial fibrillation, ventricular arrhythmias, or any other heart related disease that requires electroanatomical mapping such as cardiac pacing. More specifically, it relates to an efficient treatment of such cases using a three-dimensional electrical potential model and heat diffusion modeling.

DISCUSSION OF THE RELATED ART

Cardiac arrhythmias, and atrial fibrillation (A-fib) in particular, are life-threatening conditions in which the heart's rhythm becomes abnormal. For example, A-fib results from an abnormal depolarization of the cardiac atria and therefore irregular electrical conduction. While A-fib alone is not life threatening for most of the cases, it is now known that patients with A-fib have greater chance of stroke and death as clots are formed in the atria due to the lack of contractile motion. Incidence of A-fib is widespread in the general population and is projected to grow in the future. Treatment of A-fib generally starts with medication but where the condition is not sufficiently improved thereby, subsequent treatment may involve tissue ablation in which a section of the cardiac atria is burned with a radio-frequency ablation catheter for instance. More recent techniques like cryo-ablation or ultrasound-based devices are being explored, under the same principle of burning the muscle to cut the arrhythmogenic tissue and pathways. If successful, the burning of the cardiac atria changes the manner in which electrical impulses are transmitted through the heart and abnormal depolarization of the cardiac atria may be reduced or eliminated.

The ablation process is exceedingly long, involves a difficult recovery, and is particularly expensive and often the intervention is not successful, thereby requiring second and third interventions as arrhythmia recurrences appear.

SUMMARY

A method for guiding electrophysiology (EP) intervention using a patient-specific electrophysiology model includes acquiring a medical image of a region of interest of a patient subject (S201). A set of sparse EP signals is acquired over an anatomy of the region of interest using the acquired medical image for guidance (S202). The acquired set of sparse EP signals is interpolated using a patient specific computational electrophysiology model to generate an enlarged set of EP signals, the enlarged set of EP signals including more EP signals than the set of sparse EP signals, where the enlarged set of EP signals is used to generate a three-dimensional model of EP dynamics (S203). A rendering of the generated three-dimensional model is displayed to a user. A set of one or more candidate intervention sites is received from a user, effects on the EP dynamics within the region of interest resulting from intervention at the set of one or more candidate intervention sites is simulated using the generated three-dimensional model, and a rendering of the three-dimensional model showing the simulated effects is displayed to the user (S205).

The method may further include receiving, from the user, an indication of whether the simulated effects are acceptable (S206), and when the received indication indicates that the simulated effects are not acceptable, the steps of displaying a rendering of the generated three-dimensional model to a user, receiving, from the user, a set of one or more candidate intervention sites, simulating effects on the EP dynamics within the region of interest resulting from intervention at the set of one or more candidate intervention sites using the generated three-dimensional model, and displaying a rendering of the three-dimensional model showing the simulated effects to the user (S205), may be repeated until an indication indicating that the simulated effects are acceptable is received from the user.

The method may further include providing visual guidance to the user to perform intervention at the set of one or more candidate intervention sites (S207). The set of sparse EP signals may be re-acquired over the anatomy of the region of interest (S208). The re-acquired set of sparse EP signals may be interpolated to generate an updated enlarged set of EP signals, the updated enlarged set of EP signals including more EP signals than the re-acquired set of sparse EP signals. The three-dimensional model of EP dynamics may be updated within the region of interest using the updated enlarged set of EP signals. A rendering of the updated three-dimensional model may be displayed to the user.

The region of interest may include cardiac atria or ventricles.

The acquired medical image may be a computed tomography (CT), magnetic resonance (MR), ultrasound (US) or rotational angiography image. At least one of a left and right atria may be segmented from the acquired medical image.

Acquiring the set of sparse EP signals may include providing, to the user, one or more measurement point suggestions. The one or more measurement point suggestions may be derived from the three-dimensional model.

The interpolating of the acquired set of sparse EP signals may include using a computations model of cardiac electrophysiology.

The user may use the display of the rendering of the generated three-dimensional model to detect one more rotors or other abnormal EP patterns.

One more rotors or other abnormal EP patterns may be automatically detected from the generated three-dimensional model of EP dynamics.

The intervention may include tissue ablation using radio-frequency, micro-wave, cryo-technology or ultrasound.

The simulating of the effects on the EP dynamics may include using a heat or cold transfer model coupled with tissue viability model.

The displaying of the rendering of the three-dimensional model showing the simulated effects to the user may include illustrating one or more ablation targets, with the updated cardiac electrophysiology computed from the electrophysiology model.

The displaying of the rendering of the three-dimensional model showing the simulated effects to the user may include illustrating one or more ablation targets, without the updated cardiac electrophysiology computed from the electrophysiology model.

The method may be used to treat atrial fibrillation, atrial tachycardia, atrial flutter, ventricular tachycardia, or ventricular fibrillation.

A method for modeling cardiac atrial electrophysiology (EP), includes acquiring a medical image of atria of a patient subject (S201). A set of sparse EP signals is acquired over an anatomy of the atria using the acquired medical image for guidance (S202). The acquired set of sparse EP signals is interpolated to generate an enlarged set of EP signals, the enlarged set of EP signals including more EP signals than the set of sparse EP signals, and a three-dimensional model of EP dynamics within the atria is generated using the enlarged set of EP signals (S203).

The acquired medical image may be a computed tomography (CT), magnetic resonance (MR), ultrasound (US) or rotational angiography image.

Acquiring the set of sparse EP signals may include providing, to a user, one or more measurement point suggestions. The interpolating of the acquired set of sparse EP signals may include using a patient-specific computations model of electrophysiology.

A method for automatically detecting rotors or other abnormal electrophysiology (EP) patterns from cardiac atria includes acquiring a medical image of atria of a patient subject (S201). A set of sparse EP signals is acquired over an anatomy of the atria using the acquired medical image for guidance (S202). The acquired set of sparse EP signals is interpolated to generate an enlarged set of EP signals, the enlarged set of EP signals including more EP signals than the set of sparse EP signals, and a three-dimensional model of EP dynamics is generated within the atria using the enlarged set of EP signals (S203). One or more rotors or other abnormal EP patterns are detected from the generated three-dimensional model (S204).

The method may further include displaying a rendering of the three-dimensional model showing the detected one or more rotors or other abnormal EP patterns to a user.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
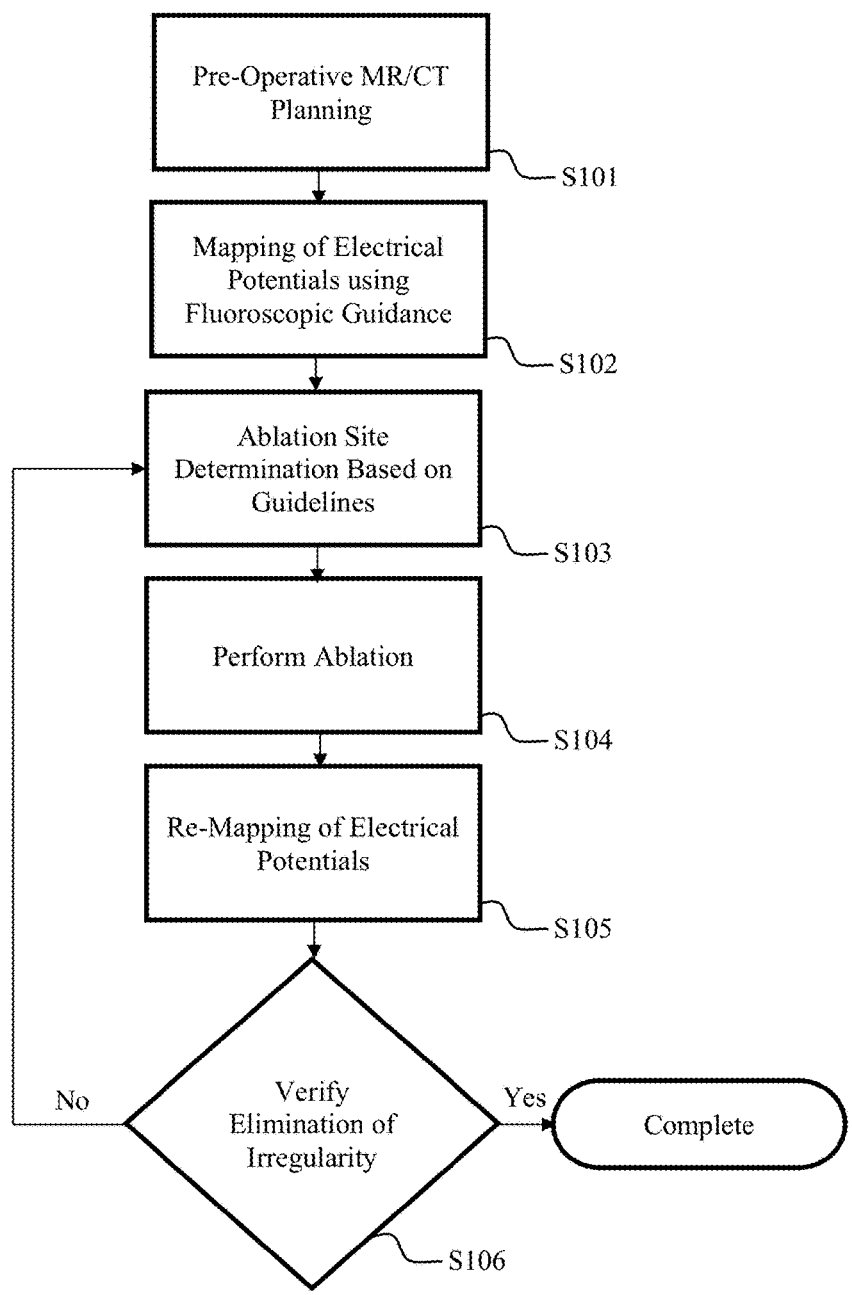
FIG. 1 is a flow chart illustrating an approach for treatment of atrial fibrillation involving ablation methods such as cryo-ablation, microwave, laser, RF, or ultrasound techniques.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention provide a novel approach for treating atrial fibrillation (A-fib), ventricular arrhythmias, performing cardiac pacing, or other cardiac diseases that require mapping and possible ablations which may reduce procedure time and increase effectiveness of intervention so that patient health may be improved and costs associated with treatment reduced. Exemplary embodiments of the present invention generate a personalized model of the electrophysiology that may be queried to test ablation candidate sites or automatically select such sites and therefore guide the electrophysiologist performing the intervention towards optimal ablation targets. The generated model may also be updated after the performance of ablation to further confirm success.

FIG. 1 is a flow chart illustrating an approach for treatment of cardiac abnormalities involving ablation. As a first step, a pre-operative magnetic resonance (MR) image, a computed tomography (CT) image or some other medical imaging study may be conducted (Step S101). The medical image, so acquired, may then be segmented to emphasize the anatomical geometry. This imagery may be used during intervention by superimposing it with real-time fluoroscopy imagery so that anatomical features which are not easily identifiable from within the fluoroscopy imagery alone may be more clearly visualized.

Thereafter, an electrophysiologist may use the combined imagery to guide a probe through the atria and detect electric charges at various regions. In this way, a detailed electrophysiology (EP) mapping is performed to assess the electrical condition of the patient (Step S102). Low voltage areas, due to fibrosis or scar tissues, may be identified. However, the resulting EP data is multi-dimensional and therefore may be difficult to interpret by those without sufficient experience. This EP study may be used to determine if the patient can be treated through ablation. It also enables the identification of ablation targets (Step S103). These targets may be chosen on an ad-hoc based on institutional guidelines. Hence, the preferred candidate sites for the exact same patient can vary based on physician and institution. Next, a first ablation round may be performed (Step S104). Catheter tracking may optionally be used in this step. The anatomical model overlay may also be employed for guiding of the ablation catheter. Once the ablations performed, another EP sensing study may be performed to verify the results of the ablation (Step S105). If effective elimination of the fibrillations is not verified (No, Step S106), then the procedure may be repeated until treatment is achieved (Yes, Step S106) at which point the intervention may be complete. The overall clinical workflow may be very time consuming, as the determination of the ablation sites and effectiveness of ablation is mostly based on the experience of the clinician and requires multiple measurements.

Exemplary embodiments of the present invention provide an enhanced workflow for treatment of atrial fibrillation, ventricular arrhythmias, or other cardiac mapping procedures that makes use of computational models of electrophysiology. Computational models of atrial electrophysiology, for example, ionic models such as the Courtemanche-Ramirez-Nattel (CRN) model, may be used to mimic the main ionic interactions giving rise to the action potential in atrial myocytes, and may be used in atrial simulations. Other models may also be used such as models that are integrated at an organ level, surface-based bi-layer modeling of atrial electrophysiology with good physiology capture range, patient-specific simulation of atrial electrophysiology based on MRI data, etc. Exemplary embodiments of the present invention may use these and other such models as part of an interventional system to guide A-fib and ablation therapy in general based on computational modeling, medical imaging and catheter tracking.

Figure 2:
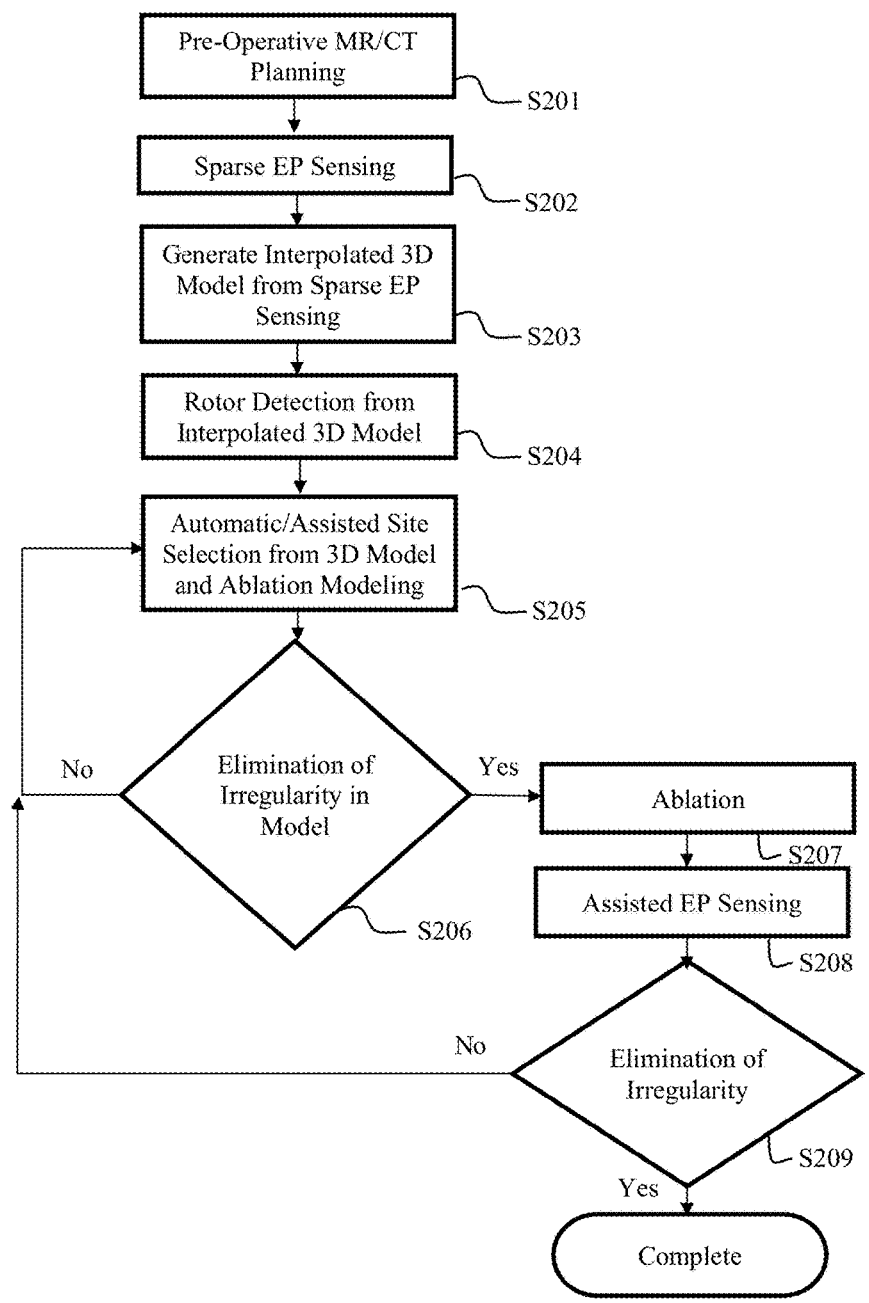
FIG. 2 is a flow chart illustrating an approach for treatment of atrial fibrillation, ventricular arrhythmias, involving ablation that makes use of EP modeling in accordance with exemplary embodiments of the present invention.

FIG. 2 is a flow chart illustrating an approach for treatment of atrial fibrillation involving RF ablation that makes use of EP modeling in accordance with exemplary embodiments of the present invention. While the instant approach is described in terms of treatment of A-fib, it is to be understood that the process described herein may be applied to atrial tachycardia, atrial flutter, ventricular tachycardia and fibrillation, and any other electrophysiology disease that could be treated through ablation therapy.

The various steps of this approach provide a workflow making use of rapid electrophysical modeling, virtual ablation, and the visualization of the depolarization to guide the electrophysiologist towards the optimal ablation targets. This new workflow may utilize a personalized computational model of cardiac electrophysiology and heat transfer, coupled with advanced image analytics and visualization.

First, pre-operative MR/CT planning images of the atria may be acquired and segmented (Step S201). Alternatively, MR/CT planning may be performed intra-operatively using, for example, an interventional MRI. Segmentation of the image data may include segmenting at least one of the left and right atria from medical images. If available, tissue fibrosis and scar may be segmenting from medical images.

Next, a sparse EP sensing protocol may be employed (Step S202). During this stage, the electrophysiologist may measure the electrical activity at only a selected set of points, as opposed to a wider set of points that may be used in conventional EP mapping. In this approach, fewer EP sensing points may be used owing to the computational model's ability to interpolate and extrapolate electrophysiology from the partial data, which is something that trained electrophysiologist would not otherwise be able to do according to the conventional approach. These points can either be manually selected or automatically determined based on the anatomical and/or scar segmentation. A computational model is then generated and used to interpolate the values over the atria so that a complete EP modeling may be generated from the sparse EP sensing data (Step S203). Interpolating sparse EP signals over atrial anatomy may be performed using a computations model.

Exemplary embodiments of the present invention may also provide automatic measurement point suggestions of sampling points that may be provided to the operator based on an estimate of data uncertainty.

The measured electrophysiological signals may then be used to detect rotors and other abnormal features (Step S204). Exemplary embodiments of the present invention may utilize an advanced visualization approach for faster identification of rotors and other abnormalities. This visualization may display a graphical representation of the generated 3D EP model, which may include a map of electrophysiology dynamics, so that the electrophysiologist may more easily identify rotors and other abnormalities by looking at a visual representation, rather than merely looking at a set of EP data. This visualization of the dynamic map may be presented in a static 3D image via a function of the dynamic map. Additionally, exemplary embodiments of the present invention may automatically identify rotor and other abnormality candidates from within the graphical representation. The automated approach may also provide candidate site selection for performing ablation.

From this visual data, the electrophysiologist may make a determination as to where to perform ablation and once an ablation target is identified, virtual ablation may be performed within the model (Step S205). This virtual ablation may be a computer simulation predicting the likely changes in electrophysiology based on ablation being performed at the identified ablation targets. Simulation of ablation may be performed, for example, by modeling heat or cold transfer. Atrial electrophysiology may then be recomputed to verify treatment success (Step S206). According to some exemplary embodiments of the present invention, different ablation options may be tested interactively within the simulation.

If the simulation results determine a successful procedure (Yes, Step S206), the operator may proceed with the intervention (Step S207) followed by a subsequent sparse EP sensing step performed for verification (Step S208). For the purpose of aiding in proper ablation, exemplary embodiments of the present invention may generating and display maps of ablation targets based on the results of the computational model, along with computed electrocardiograms.

EP sensing performed after ablation, according to some exemplary embodiments of the present invention, may use the same set of sparse sample points used in the sparse EP sensing step described above (Step S202). However, according to other exemplary embodiments of the present invention, a subset of EP sensing points may be automatically determined based on an assessment of where EP has likely been changed and a determination of a minimum number of points needed to know or infer EP changes.

The results of the EP sensing may be fed back into the EP model, extrapolation and interpolation may be performed, and the electrophysiologist may determine, for example, based on an updated graphical interpretation of the model, whether the fibrillations have been successfully treated (Step S209). If they have (Yes, Step S209) then the intervention may be completed, otherwise (No, Step S209), the procedure may be iterated until the physician determines that the fibrillations have been eliminated (Yes, Step S209). Furthermore, the model may be progressively refined as more data is acquired.

Figure 3:
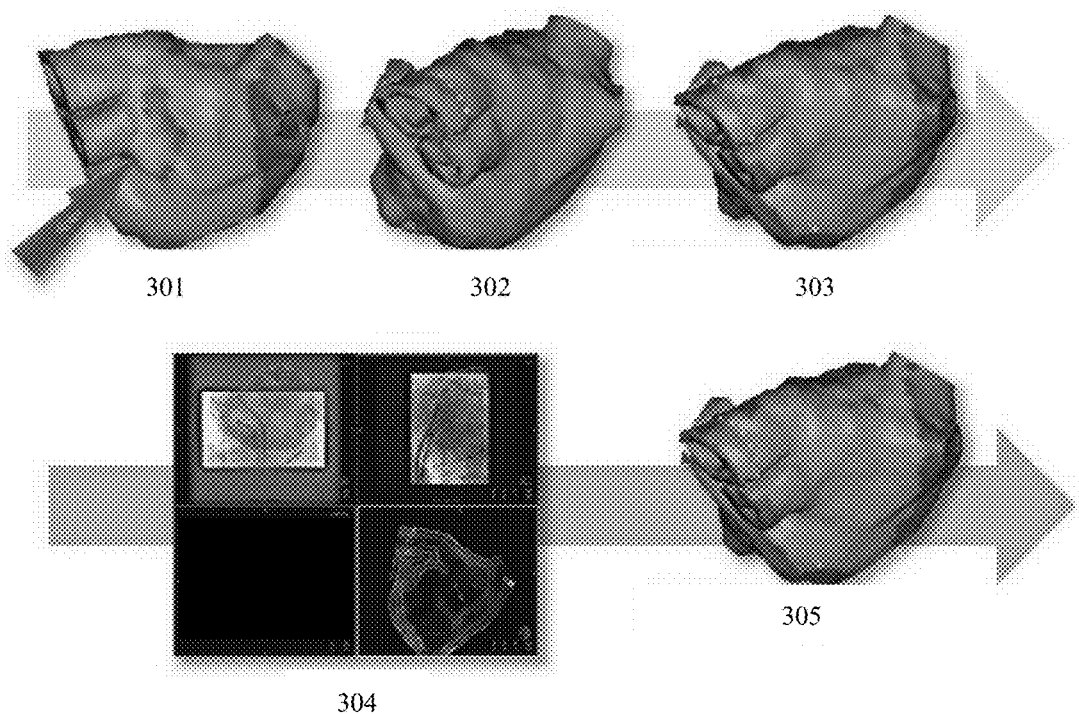
FIG. 3 is a diagram providing a visual representation of various steps for performing a workflow for EP procedures in accordance with exemplary embodiments of the present invention.

FIG. 3 is a diagram providing a visual representation of various steps for performing a workflow for EP procedures as described above. Illustration 301 represents an EP map obtained along with the electrical model of the heart. The visualization in a cine sequence or one of the proposed visualization methods allows the physician to locate rotors and other defects related to A-fib. Illustration 302 represents planned sites for ablation that may be marked on the heart model. Illustration 303 represents a recomputed model, post ablation, which shows that the rotor has been eliminated. Illustration 304 represents an image of an actual ablation that occurs based on the planned sites. Here the marked ablation points may be shown with a color-shaded model of the heart. The catheter may then be tracked and guided to the determined ablation targets. Another round of EP mapping may then be performed to verify the rotor elimination, as is shown in illustration 305.

As described above, while conventional approaches for manual rotor detection involved EP sensing at all possible sites to properly understand EP signals through the atria, exemplary embodiments of the present invention may rely on sparse EP signal sampling. According to exemplary embodiments of the present invention, sparse EP sensing may utilize two consecutive steps that could be iterated for increased precision: 1) EP sensing at tracked catheter locations and 2) dense EP map reconstruction. This inventive approach may: 1) not require a separate electromagnetic tracking system for locating the tip of the sensing catheter, and 2) the sensing time may be reduced by doing a "model-based" interpolation among the collected data, which include 3D positions and the EP signal.

In performing EP sensing in accordance with exemplary embodiments of the present invention, first, the EP sensing catheter tip may be reconstructed using a bi-plane x-ray system or magnetic catheter tracking system. Next, a detailed anatomical model of the atria may be estimated from the registered 3D image (CT, MRI). Machine learning coupled with advanced graph-based methods may be employed to estimate the anatomy. If interventional MRI is available, scar and fibrosis may be segmented from the image and mapped to the model. Finally, a model of fiber orientation may be generated on the anatomical model based on histological studies, like for the ventricles. If available, in-vivo diffusion tensor imaging may be used as well since the framework may accept tensors as fiber orientation.

Third, the set of reconstructed points along with the corresponding EP signals may be used to build a dense EP map based on a) registered pre-operative model of the atria (left, right or both) e.g., from CT or MR, and b) model of EP propagation. To that end, the EP signal measured at each catheter locations may be mapped to the anatomical model. Then, a fast, near real-time atrial electrophysiology model may be employed to calculate potential propagation throughout the anatomy. According to an exemplary embodiment of the present invention, the LBM-EP method may be employed. According to another exemplary embodiment, graph-based approaches may be used. Features of the various exemplary embodiments described herein may also be combined.

Using generic model parameters however might not yield accurate extrapolation maps due to changes in physiology between patients. An estimation procedure is therefore performed as follows: Given an initial set of N points, N small, the electrical properties of the atrium may be automatically estimated such that the computed electrical properties at these points match the measurements. For example, activation times may be matched by estimating tissue electrical conductivity. According to an exemplary embodiment of the present invention, the estimation procedure may be performed using inverse modeling, but machine learning techniques may additionally or alternatively be used. At the end of the process, the computed EP at the N points may match the measurements. However, the correctness of the value beyond the N measurements might not be guaranteed. In a second step thus, EP measurements may be performed at K additional points, and the model may be updated for increased accuracy. Accordingly, through the model, the user may be able to identify the region of interest where higher accuracy is needed (e.g. close to rotors). As a result, EP sensing is done sparsely but is also targeted, therefore shortening the acquisition time.

According to another exemplary embodiment of the present invention, the model estimated from the N initial point may be used to estimate fitting uncertainty. This estimated uncertainty information may then be used to guide subsequent measurement points for increased accuracy.

After model fitting, the model is used to extrapolate the potential values over the atrial surface, which are displayed by a system such as that described below.

As discussed above, exemplary embodiments of the present invention may provide an approach for virtual ablation and rotor detection. Once the EP signal is acquired and the model personalized, virtual ablation may be performed to identify the optimal ablation strategy. This step may be performed either automatically or interactively. For example, in the interactive approach, the operator may select the positions on the atria to ablate. In the automatic approach, for example, the anatomy may be "scanned" to identify the optimal ablation targets. This stands in contrast to prior approaches in which the operator or physician, looking at EP data, follows local guidelines based on the results of the EP-Study without the use of interpolated data or any simulation.

Figure 4:
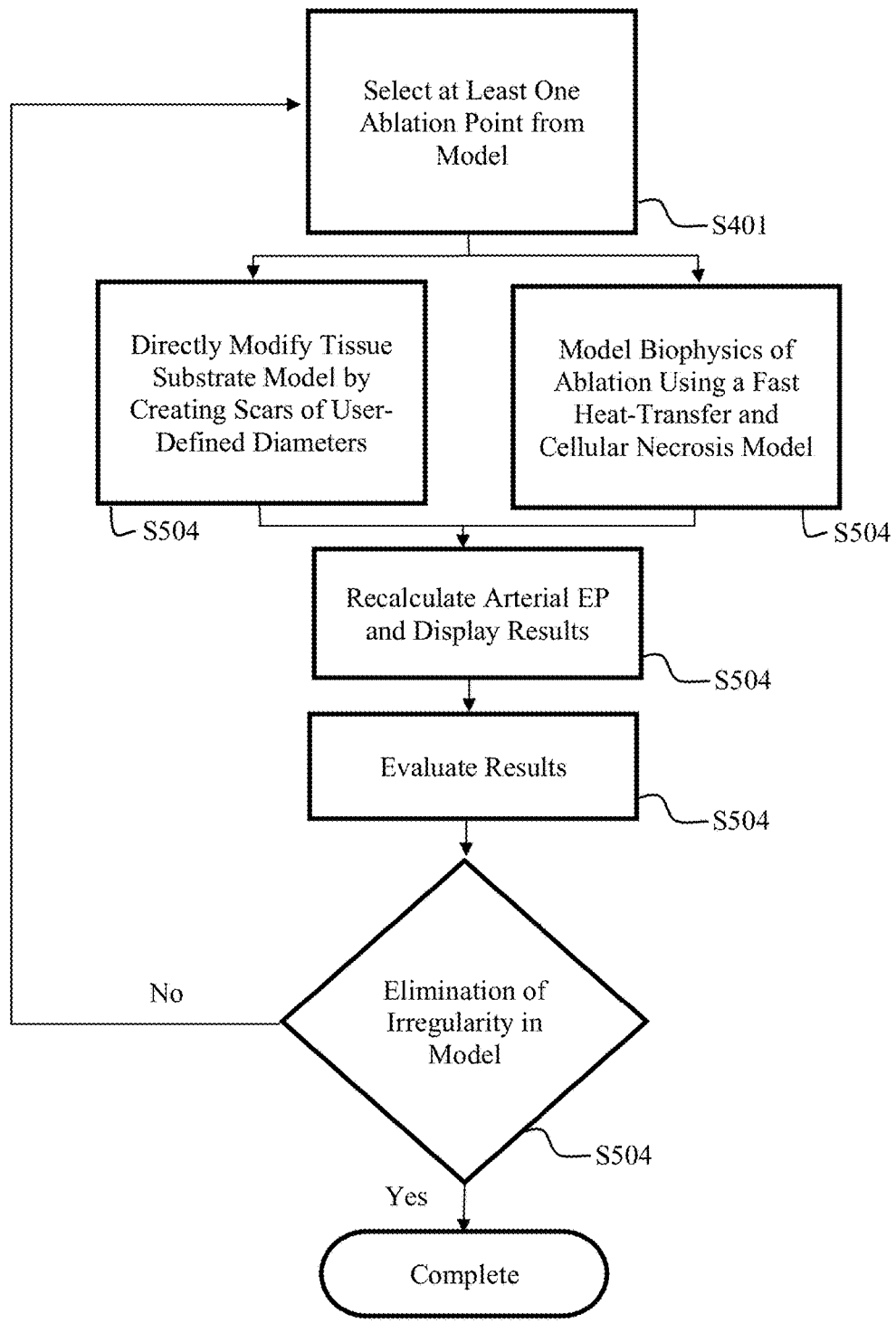
FIG. 4 is a flow chart illustrating an approach for virtual ablation and rotor detection in accordance with exemplary embodiments of the present invention.

FIG. 4 is a flow chart illustrating an approach for virtual ablation and rotor detection in accordance with exemplary embodiments of the present invention. First, at least one ablation point may be selected on the model (Step S401). Thereafter, a simulated ablation may be generated at each of the selected ablation points. This may be performed in multipole ways. According to one approach, a tissue substrate model may be directly modified by creating scars of user-defined diameters. The modeled scars may be set to have no electrical conductivity (Step S402). Alternatively, the biophysics involved in ablation may be modeled (Step S403). To that end, a fast heat-transfer and cellular necrosis model may be used.

Regardless of how the ablations are simulated, thereafter, atrial electrophysiology may be recalculated and the resulting potential maps and electrocardiogram may be displayed (Step S404). The resulting may can then be used to evaluate the effects of the ablation points on the patient (Step S405). In the case of all ablation points being modeled, the final outcome of the procedure may be modeled. Moreover, in addition to RF ablations, dragging ablations, microwave ablations, and cryo-balloon ablations may also be simulated using this process. Additionally, difficult to access or regions that may be sensitive, for example, due to nearby structures, that may require lower ablation energy may also be simulated in accordance with this approach.

The evaluated results may be used to determine whether the fibrillations may likely be eliminated by ablation to the selected ablation points (Step S506). The process may complete if the evaluated results show adequate elimination (Yes, Step S506) whereas the simulation may be iterated if the evaluated results fail to show adequate elimination (No, Step S506).

As described above, exemplary embodiments of the present invention provide an approach for using a model to visualizing atrial EP so that rotors and other abnormalities may be more easily detected. Exemplary embodiments of the present invention may also extend this approach to visualizing atrial EP to confirm success of ablation. According to such an approach, a bi-plane x-ray system or magnetic catheter tracking may be used to reconstruct the location of the ablation catheter at the time close to when the ablation is performed (e.g., right before, during, or right after). The location of ablation catheter may then be placed in the context of a pre-operative model (e.g. from CT or MR), and the conductivity of the EP model at the vicinity of this point may be modified to reflect the tissue substrate modification due to the ablation. The modification could for example be reflected as a change in the conductivity of tissue near the ablated location. The geometrical extent of the change could be considered as a function of time (e.g., ablation duration) and pressure that physician exerts on the catheter. A model of heat transfer could also be used to accurately calculate the extent of ablation. Additional data afforded though force-sensing catheters may be used to more precisely compute the energy delivered to the tissue. Finally, catheter shape and cryo-ablations may be considered as factors for tissue conductivity changes.

According to such an embodiment, the dense EP map may be reconstructed using the "modified" model and may be immediately visualized. The visualization of the recomputed dense EP map need not reflect the ablation site, and may further be tuned or refined based on additional sparse EP measurements.

Regardless of the approach used, exemplary embodiments of the present invention provide techniques for visualizing multi-dimensional EP data in a manner that facilitates detection of problems and may be used to gauge effectiveness of treatment. In general, the multi-dimensional EP data created from the EP-map may require an experienced reader to appropriately determine the type of fibrillation and the location of rotors that should be ablated. To facilitate this process, exemplary embodiments of the present invention provide several methods to condense the data to a format simpler to comprehend.

Figure 5:
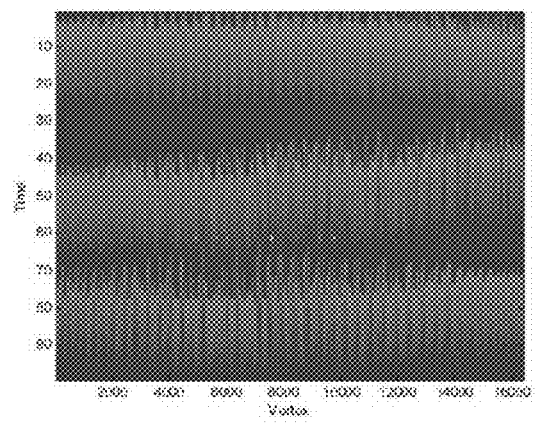
FIG. 5 provides a pair of graphs illustrating EP values as a function of time while removing immediate spatial information, as may be used in accordance with exemplary embodiments of the present invention.
Figure 5:
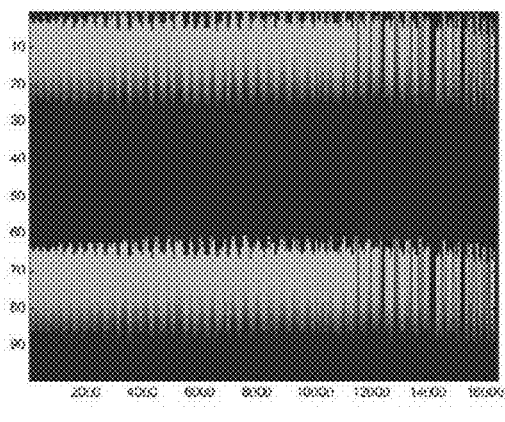

FIG. 5 provides a pair of graphs illustrating EP values as a function of time while removing immediate spatial information, as may be used in accordance with exemplary embodiments of the present invention. Some spatial information may still be retained by keeping nearby points close to each other in the graph. The comparison of the image 501 and 502 may show that an abnormality exists. For example, a single 2D image encompassing the entire model may be viewed to locate abnormalities. Note that the blank lines in image 502 suggest a complete lack of conductance due to ablation or other factors. In this particular case, these locations may be sites where ablations is simulated.

Figure 6:
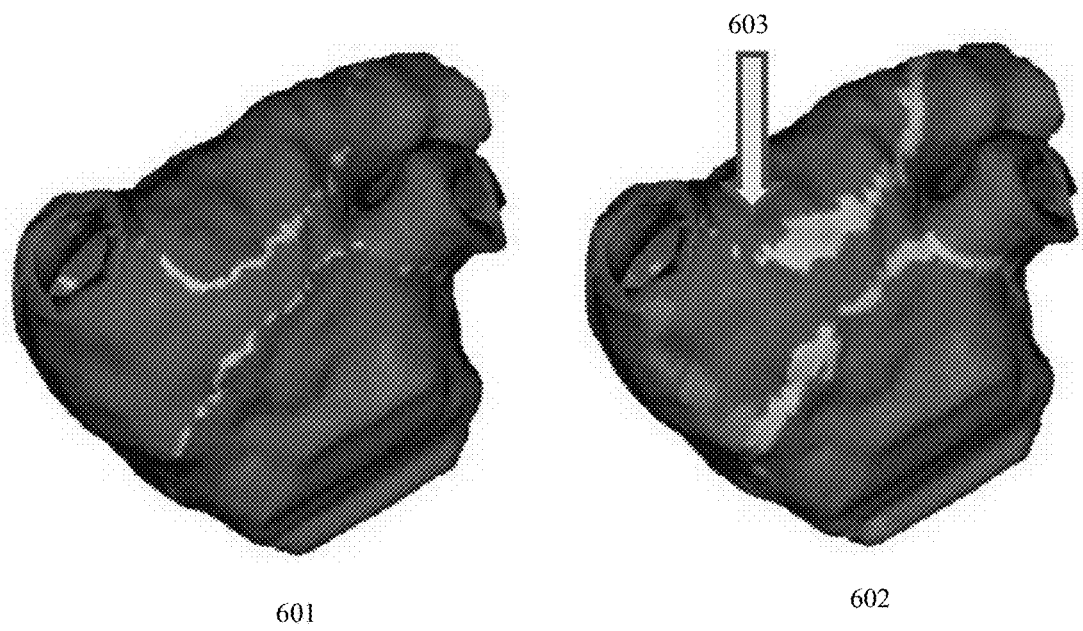
FIG. 6 provides a pair of renderings showing a 3D model of the heart with potential fronts overlaid.

FIG. 6 provides a pair of renderings showing a 3D model of the heart with potential fronts overlaid. Proposed 3D visualization of multiple time potential fronts. Time series information is captured along with spatial information in a single 3D view. The shade of each front is temporal based. In rendering 601, a normal atrial depolarization is shown across beats. The smooth depolarization is visible with two fronts of different shades. Note that the fronts are aligned and do not intersect, implying a uniform depolarization. However, in rendering 602, an atrial fibrillation is simulated. The fronts intersect and the non-uniformity is apparent. The arrow 603 signifies the location of a rotor and also the location where multiple fronts intersect. The fronts may be automatically selected based on gradient information at a select position in the image.

Similar visualizations may also be obtained by visualizing the depolarization times across several beats. Although not shown, dynamic and static rotors may be visualized on the 3D model as a moving hurricane front as shown in weather forecasts.

Additionally, exemplary embodiments of the present invention may be used to track dynamic rotors and perform quantitative pattern analysis in a manner similar to what is done in weather mapping, where a rotor would be analogous to a hurricane, for example, to provide a non-dynamic visualization of the dynamic data.

Exemplary embodiments of the present invention may also facilitate the use of basket catheters for electrophysiology mapping. Projecting the EP information on the anatomical model may be performed as follows. First, the basket catheter may be identified on bi-plane angiograph, in a similar way as for the ablation catheters. The 3D position of the basket may be registered in the anatomical model, and a CAD model of the basket may be registered. Alternatively, or additionally, the basket may be directly segmented from the image. Next far field theory may be used to map back the potential on the anatomical model. In this regard, three methods are contemplated: 1) closest point mapping, 2) mapping along the Laplacian streamlines between the catheter surface and the atrial model, and 3) using models of potential conduction in blood media to map the measured potentials from the basket to the anatomy.

Exemplary embodiments of the present invention may also use body surface mapping or ECG. Simple back-projection with Tikhonov regularization may be employed along with more advanced inverse problem approaches. For the latter option, the LBM-EP algorithm may be coupled with a model of potential propagation in the body to calculate body surface potentials. An optimization procedure is then employed to estimate the parameters of the EP model (typically electrical conductivity, action potential duration among others) such that calculated body potentials match measured ones (e.g. through sum of squared distances). The optimization may be performed using gradient-free methods (e.g. employing NEUWOA). More advanced machine learning methods may also be used.

Exemplary embodiments of the present invention may also be expanded by performing one or more of the following: Cryo-balloon catheters may be simulated and ablations may be "dragged" to simulate a larger effected ablated region. Force-sensing ablation catheters may be integrated to help determine and then simulate the effective energy delivered to the tissue. Esophagus position or other sensitive structures with known access difficulty may be simulated to warn the user of ablation points that may not be performed at full energy or effectiveness. Less effective/accessible ablation sites may be considered in determining the complete list of planned ablation sites.

Figure 7:
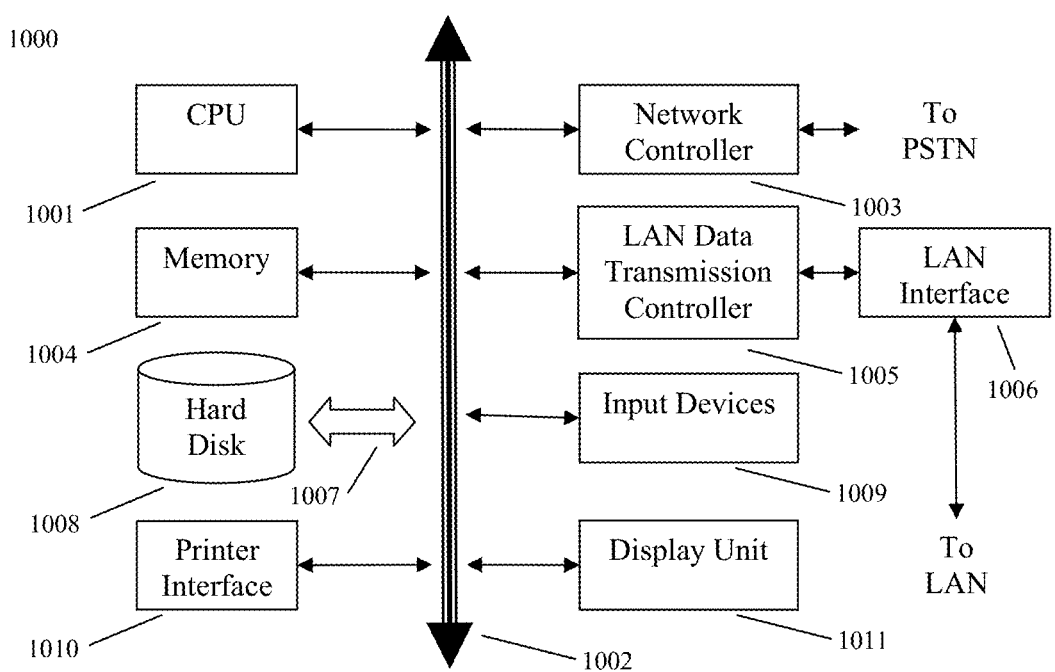
FIG. 7 shows an example of a computer system capable of implementing the method and apparatus according to embodiments of the present disclosure.

FIG. 7 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for guiding electrophysiology (EP) intervention using a patient-specific electrophysiology model, comprising:
   acquiring a medical image of a region of interest of a patient subject;
   acquiring a set of sparse EP signals over an anatomy of the region of interest using the acquired medical image for guidance;
   interpolating the acquired set of sparse EP signals using a patient specific computational electrophysiology model to generate an enlarged set of EP signals, the enlarged set of EP signals including more EP signals than the set of sparse EP signals;
   generating a three-dimensional model of EP dynamics within the region of interest using the enlarged set of EP signals;
   displaying a rendering of the generated three-dimensional model to a user;
   receiving, from the user, a set of one or more candidate intervention sites;
   simulating effects on the EP dynamics within the region of interest resulting from intervention at the set of one or more candidate intervention sites using the generated three-dimensional model; and
   displaying a rendering of the three-dimensional model showing the simulated effects to the user.

2. The method of claim 1, further comprising:
   receiving, from the user, an indication of whether the simulated effects are acceptable, and when the received indication indicates that the simulated effects are not acceptable, repeating the steps of:
      displaying a rendering of the generated three-dimensional model to a user;
      receiving, from the user, a set of one or more candidate intervention sites;
      simulating effects on the EP dynamics within the region of interest resulting from intervention at the set of one or more candidate intervention sites using the generated three-dimensional model; and
      displaying a rendering of the three-dimensional model showing the simulated effects to the user, until an indication indicating that the simulated effects are acceptable is received from the user.

3. The method of claim 2, further comprising:
   providing visual guidance to the user to perform intervention at the set of one or more candidate intervention sites;
   re-acquiring the set of sparse EP signals over the anatomy of the region of interest;
   interpolating the re-acquired set of sparse EP signals to generate an updated enlarged set of EP signals, the updated enlarged set of EP signals including more EP signals than the re-acquired set of sparse EP signals;
   updating the three-dimensional model of EP dynamics within the region of interest using the updated enlarged set of EP signals; and
   displaying a rendering of the updated three-dimensional model to the user.

4. The method of claim 1, wherein the region of interest includes cardiac atria or ventricles.

5. The method of claim 1, wherein the acquired medical image is a computed tomography (CT), magnetic resonance (MR), ultrasound (US) or rotational angiography image.

6. The method of claim 5, wherein at least one of a left and right atria are segmented from the acquired medical image.

7. The method of claim 1, wherein acquiring the set of sparse EP signals includes providing, to the user, one or more measurement point suggestions.

8. The method of claim 7, wherein the one or more measurement point suggestions are derived from the three-dimensional model.

9. The method of claim 1, wherein the interpolating of the acquired set of sparse EP signals includes using a computations model of cardiac electrophysiology.

10. The method of claim 1, wherein the user uses the displaying of the rendering of the generated three-dimensional model to detect one more rotors or other abnormal EP patterns.

11. The method of claim 1, wherein one more rotors or other abnormal EP patterns are automatically detected from the generated three-dimensional model of EP dynamics.

12. The method of claim 1, wherein the intervention includes tissue ablation using radio-frequency, micro-wave, cryo-technology or ultrasound.

13. The method of claim 1, wherein the simulating of the effects on the EP dynamics includes using a heat or cold transfer model coupled with tissue viability model.

14. The method of claim 1, wherein the displaying of the rendering of the three-dimensional model showing the simulated effects to the user includes illustrating one or more ablation targets, with updated cardiac electrophysiology computed from the electrophysiology model.

15. The method of claim 1, wherein the displaying of the rendering of the three-dimensional model showing the simulated effects to the user includes illustrating one or more ablation targets, without updated cardiac electrophysiology computed from the electrophysiology model.

16. The method of claim 1, wherein the method is used to treat atrial fibrillation, atrial tachycardia, atrial flutter, ventricular tachycardia, or ventricular fibrillation.

17. A method for modeling cardiac atrial electrophysiology (EP), comprising:
   acquiring a medical image of an atria of a patient subject;
   acquiring a set of sparse EP signals over an anatomy of the atria using the acquired medical image for guidance;
   interpolating the acquired set of sparse EP signals to generate an enlarged set of EP signals, the enlarged set of EP signals including more EP signals than the set of sparse EP signals;
   generating a three-dimensional model of EP dynamics within the atria using the enlarged set of EP signals; and
   simulating effects on the EP dynamics within the atria resulting from an intervention using the generated three-dimensional model.

18. The method of claim 17, wherein the acquired medical image is a computed tomography (CT), magnetic resonance (MR), ultrasound (US) or rotational angiography image.

19. The method of claim 17, wherein acquiring the set of sparse EP signals includes providing, to a user, one or more measurement point suggestions.

20. The method of claim 17, wherein the interpolating of the acquired set of sparse EP signals includes using a patient-specific computations model of electrophysiology.

21. A method for automatically detecting rotors, comprising:
- acquiring a medical image of an atria of a patient subject;
- acquiring a set of sparse electrophysiology (EP) signals over an anatomy of the atria using the acquired medical image for guidance;
- interpolating the acquired set of sparse EP signals to generate an enlarged set of EP signals, the enlarged set of EP signals including more EP signals than the set of sparse EP signals;
- generating a three-dimensional model of EP dynamics within the atria using the enlarged set of EP signals;
- detecting one or more rotors from the generated three-dimensional model; and
- simulating effects on the EP dynamics within the atria resulting from an intervention for the detected one or more rotors using the generated three-dimensional model.

22. The method of claim 21, further including displaying a rendering of the three-dimensional model showing the detected one or more rotors to a user.

* * * * *